United States Patent [19]
Brayton et al.

[11] Patent Number: 5,932,174
[45] Date of Patent: *Aug. 3, 1999

[54] DEVICE FOR CHLORIDE ION REMOVAL PRIOR TO CHEMICAL OXYGEN DEMAND ANALYSIS

[75] Inventors: Scott Vance Brayton, Ames; Donald Gene Miller, Slater, both of Iowa

[73] Assignee: Hach Company, Loveland, Colo.

[*] Notice: This patent is subject to a terminal disclaimer.

[21] Appl. No.: 08/866,466

[22] Filed: May 30, 1997

Related U.S. Application Data

[63] Continuation of application No. 08/533,318, Sep. 25, 1995, Pat. No. 5,667,754.

[51] Int. Cl.$^6$ .................................................. G01N 33/18
[52] U.S. Cl. ............................. 422/79; 422/61; 422/101; 422/59; 436/62; 436/145; 436/146; 436/175
[58] Field of Search .................................. 422/59, 60, 70, 422/72, 79, 101, 61; 436/62, 145, 146, 166, 175, 177, 178, 183; 210/266, 282, 283

[56] References Cited

U.S. PATENT DOCUMENTS

| | | | |
|---|---|---|---|
| 956,332 | 4/1910 | Fuller | 210/474 |
| 3,337,451 | 8/1967 | Calman | 210/683 |
| 3,346,617 | 10/1967 | Hiroki et al. | 260/465.3 |
| 3,387,038 | 6/1968 | Koch | 260/604 |
| 3,583,230 | 6/1971 | Patterson | 422/70 X |
| 3,608,736 | 9/1971 | Wong | 210/477 |
| 3,763,879 | 10/1973 | Jaworek | 210/266 X |
| 3,787,334 | 1/1974 | Yamada | 252/468 |
| 4,131,526 | 12/1978 | Moeglich | 204/149 |
| 4,234,317 | 11/1980 | Lucas et al. | 422/101 X |
| 4,241,216 | 12/1980 | Bergman et al. | 560/99 |
| 4,425,438 | 1/1984 | Bauman et al. | 422/59 X |
| 4,447,405 | 5/1984 | Ahn et al. | 423/88 |
| 4,485,015 | 11/1984 | Smith | 210/455 |

(List continued on next page.)

FOREIGN PATENT DOCUMENTS

| | | |
|---|---|---|
| 45320 | 2/1982 | European Pat. Off. . |
| 3529670 | 2/1987 | Germany . |
| 4125627 | 2/1993 | Germany . |
| 54-31792 | 3/1979 | Japan . |
| 55-2959 | 1/1980 | Japan . |
| 58-161895 | 9/1983 | Japan . |
| 58-205899 | 11/1983 | Japan . |
| 59-179187 | 10/1984 | Japan . |
| 60-218098 | 10/1985 | Japan . |
| 60-219598 | 11/1985 | Japan . |

OTHER PUBLICATIONS

Begemann et al., Bi$_4$O$_7$, Das Erste Definierte Binäre Bismut(III,V)–Oxid, Jul., 1989, pp. 123–127.

M.H. Ford–Smith et al., Kinetics of Oxidation–Reduction Reactions Between Elements of Groups V and VII. Part I. Bismuth(v) . . . , 1973, pp. 461–464, J.C.S. Dalton.

Habib Firouzabadi et al., Zinc Bismuthate Zn(BiO$_3$)$_2$ I.A. Useful Oxidizing Agent for the Efficient Oxidation . . . , Apr. 1992, pp. 1131–1134, The Chemical Society of Japan.

Membrane Filtration—Chromatography Catalog, Amicon, Inc., Publication No. 387, 1995, Amicon, Inc.

V.S. Rogov et al., Chemical Abstr., 1984, 100, 167338m.

F.P. Treadwell, et al., "Analytical Chemistry", Ed. 1930, John Wiley & Sons, Inc., NY pp. 222–227.

W. Rigby, J. Chem. Soc., 1950, 1907–1913.

V.S. Rogov, Razved, Okhr. Nedr. 1984, 58–59.

M. Namiki et al. Fresenius J. Anal. Chem., 1992, 344, 265–268.

*Primary Examiner*—Arlen Soderquist
*Attorney, Agent, or Firm*—Zarley, McKee, Thomte, Voorhees & Sease

[57] ABSTRACT

A method of pretreating aqueous chemical oxygen demand (COD) samples to remove the risk of potential chloride ion interference. The method comprises acidifying an aqueous COD test sample, and thereafter passing the acidified sample through a source of pentavalent bismuth (Bi$^{5+}$) such as sodium bismuthate.

3 Claims, 1 Drawing Sheet

U.S. PATENT DOCUMENTS

| | | | |
|---|---|---|---|
| 4,683,058 | 7/1987 | Lyman et al. | 422/100 X |
| 4,787,971 | 11/1988 | Donald | 422/101 X |
| 4,832,842 | 5/1989 | Limb | 210/249 |
| 4,859,336 | 8/1989 | Savas et al. | 210/416.1 |
| 4,863,610 | 9/1989 | Campbell | 422/70 X |
| 4,956,298 | 9/1990 | Diekmann | 422/101 X |
| 5,055,409 | 10/1991 | Aström | 436/52 |
| 5,076,922 | 12/1991 | Deare | 210/282 |
| 5,104,529 | 4/1992 | Becker | 210/195.1 |
| 5,145,789 | 9/1992 | Corti et al. | 422/60 X |
| 5,167,818 | 12/1992 | Iana et al. | 210/474 |
| 5,186,830 | 2/1993 | Rait | 210/232 |
| 5,219,529 | 6/1993 | Ngo et al. | 422/102 |
| 5,264,184 | 11/1993 | Aysta et al. | 422/101 |
| 5,304,305 | 4/1994 | Lehrer | 210/346 |
| 5,368,729 | 11/1994 | Stefkovich et al. | 210/266 |
| 5,411,661 | 5/1995 | Heiligman | 210/264 |
| 5,439,593 | 8/1995 | Price | 210/660 |
| 5,552,325 | 9/1996 | Nochumson et al. | 422/70 X |
| 5,667,754 | 9/1997 | Brayton et al. | 422/61 |

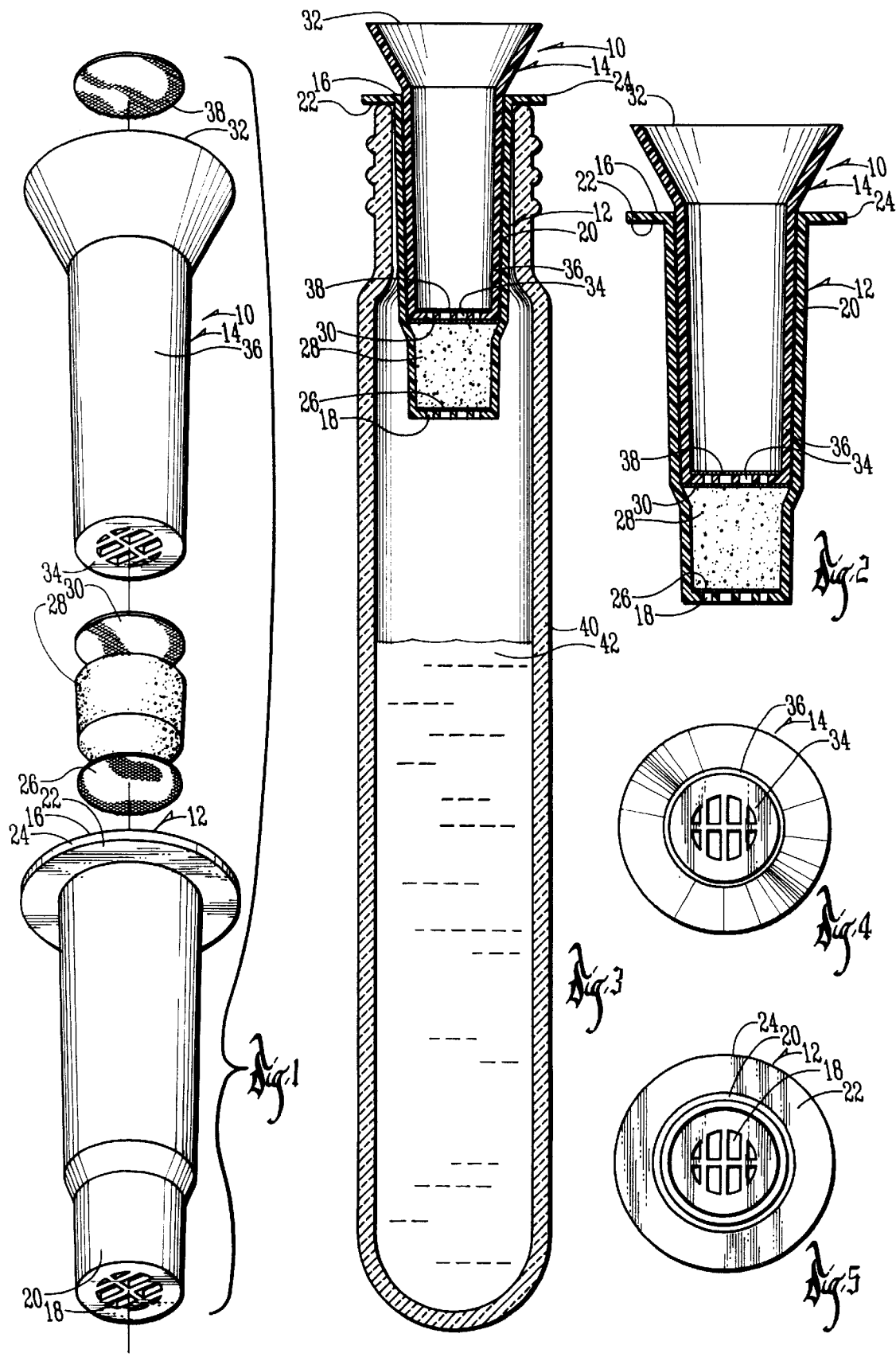

DEVICE FOR CHLORIDE ION REMOVAL PRIOR TO CHEMICAL OXYGEN DEMAND ANALYSIS

This is a continuation of application(s) Ser. No. 08/533,318 filed on Sep. 25, 1995 and which designated the U.S. Pat. No. 5,667,754.

FIELD OF THE INVENTION

The field of the present invention relates to tests for determination of Chemical Oxygen Demand (COD) in aqueous samples. More particularly, it relates to a method of removal of chloride ion from COD test samples, so that the chloride ion does not cause an erroneous high sample reading.

BACKGROUND OF THE INVENTION

Oxygen demand is an important parameter for determining the effect of organic pollutants on receiving water. As microorganisms in the environment consume these materials, oxygen is depleted from the water. This can have an adverse effect on fish and plant life.

There are three main methods of measuring oxygen demands: directly, by biochemical oxygen demand (BOD) and/or chemical oxygen demand (COD), and indirectly by total organic carbon (TOC) procedures. BOD, because it uses microorganisms for oxidation, gives the closest picture of the biological processes occurring in a stream. However, results are not available for five days, and the BOD test is inadequate as an indicator of organic pollution when used with industrial waste water containing toxic materials which poison the microorganisms and render them unable to oxidize wastes.

Unlike BOD, the two other methods do not use biological processes, and are therefore faster and not affected by toxic materials. A strong oxidizing agent or combustion technique is used under controlled conditions in the TOC method to measure the total amount of organic material in a sample. The results obtained may not be as accurate as the results reached through the COD or BOD method in predicting environmental oxygen demand because oxygen demands may differ between compounds with the same number of organic carbons in their structures. The difference in oxygen demand between two compounds containing the same amount of organic carbon can be seen in the following equations showing the oxidation of oxalic acid and ethanol:

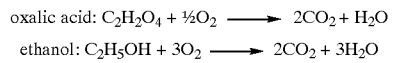

oxalic acid: $C_2H_2O_4 + \frac{1}{2}O_2 \longrightarrow 2CO_2 + H_2O$ ethanol: $C_2H_5OH + 3O_2 \longrightarrow 2CO_2 + 3H_2O$ Each molecule of ethanol uses up six times as much oxygen as an equivalent amount of oxalic acid, and thus would have a much greater effect on the dissolved oxygen present in a receiving water. Estimating environmental oxygen demand (as with BOD and COD) requires complete oxidation of carbon and hydrogen present in the organic matter. Thus, while TOC is a more direct expression of total organic content than BOD or COD, it does not provide the same kind of information. An empirical relationship can exist between TOC, BOD and COD, but the specific relationship must be established for a specific set of sample conditions.

Currently, the COD test has a fairly specific and universal meaning: the oxygen equivalent of the amount of organic matter oxidizable by potassium dichromate in a 50% sulfuric acid solution. Generally, a silver compound is added as a catalyst to promote the oxidation of certain classes of organics. Typically, a mercuric compound may be added to reduce interference from the oxidation of chloride ions by the dichromate which will give false high COD readings. The end products of organic oxidations are carbon dioxide and water.

After the oxidation step is completed, the amount of dichromate consumed is determined either titrimetrically or calorimetrically. Either the amount of dichromate reduced (Chromium III) or the amount of unreacted dichromate (Chromium VI) remaining can be measured. If the latter method and colorimetry are chosen, the analyst must know the precise amount of dichromate added and be able to set the instrument wavelength very accurately, since readings are routinely taken on the "shoulder" of the Chromium VI absorbance peak. Wavelength settings must be reproduced precisely in order to avoid errors when using a previously generated calibration curve.

Dichromate was first used in the COD test over 50 years ago. Before that time, potassium permanganate was the oxidant of choice. Analysts have tried many other reagents, such as potassium persulfate, cerium sulfate, potassium iodate and oxygen itself. Generally these other oxidants have not been satisfactory.

A prior case of this same inventor; U.S. Ser. No. 08/475,187, filed Jun. 7, 1995, and entitled "Manganese III Method For Chemical Oxygen Demand Analysis", relates to a new COD test that eliminates the use of dichromate in sulfuric acid and replaces it with another COD test reagent containing $Mn^{+3}$ ions and of improved performance. The subject matter of that application is incorporated herein by reference.

As mentioned previously, the current state of the art involves the addition of mercuric compounds added to reduce interference from the oxidation of chloride ions by the dichromate. The addition of mercuric salts, while satisfactory to eliminate interference from chloride ion in aqueous COD samples, is itself unsatisfactory because mercury is a pollutant and known toxicant, which makes it undesirable for use in COD analysis. Mercury has its own polluting and environmental risks. There is, therefore, a present and continuing need for the development of a means of removing potentially interfering chloride ions from aqueous COD samples which avoids use of mercury salts, and which does not in any way interfere with the accuracy of the COD analytical procedure. This invention has as its primary objective the fulfillment of this need.

An additional objective is to provide a cartridge device which can be provided in a kit for chemical COD analysis that can be conveniently used by operators to conduct a pretreatment chloride removal step prior to analysis of an aqueous COD sample.

The method and means of accomplishing each of the above objectives will become apparent from the detailed description of the invention which follows.

BRIEF DESCRIPTION OF THE DRAWINGS

FIG. 1 is a perspective and exploded view of the cartridge of the present invention with the inner and outer sections aligned for mating relationship.

FIG. 2 shows the inner and outer sections in mating relationship.

FIG. 3 shows in cross section a complete cartridge unit inserted in a test tube.

FIG. 4 shows a bottom view of the inner cartridge.

FIG. 5 shows a bottom view of the outer cartridge.

SUMMARY OF THE INVENTION

The invention relates to a method of pretreating aqueous COD samples to remove interference from chloride ions. Bromide and iodide ions are also removed, but they are not normally present in aqueous COD samples in concentrations high enough to constitute significant interference. In the method, the aqueous sample is acidified with a mineral acid, preferably sulfuric acid, and then passed through a source of bismuthate or other pentavalent Bismuth-containing ion or compound, preferably in solid form. After this pretreatment the sample is then used for COD analytical testing. In another aspect of a related invention, the process is conducted using inner and outer cartridges adapted to matingly fit within each other to form a cartridge unit. Both cartridges are made of materials that are inert to acidified test samples, any chloride present or chlorine generated, and not retain any organics present in the test sample and have open upper ends and a porous lower end. The outer cartridge contains solid form sodium bismuthate which may be mixed with a filter aid, and the inner cartridge contains a removable filter which may be removed and added to the COD test sample so that solid organics filtered out during the pretreatment process are recombined with the liquid portion of the sample so that the COD test results represent the total of soluble plus insoluble organic compounds and/or mixtures, yielding a test result representative of the total COD of the sample.

DETAILED DESCRIPTION OF THE INVENTION

In accordance with the process of this invention, a typical aqueous COD test sample is pretreated to remove interference from chloride ion. The pretreatment involves materials which avoid the conventional prior art treatment with mercury salts as used to complex chloride ion and render it unavailable for reaction in the COD test. In the present process the pretreatment involves reacting an acidified aqueous COD sample with a source of bismuthate ion or other pentavalent bismuth source.

The source of bismuthate or pentavalent bismuth ion is not critical, and it may be bismuth tetroxide, bismuth pentoxide, free bismuthic acid, or, more preferably, a Group I or Group II bismuthate salt. The most preferred are Group I bismuthate salts, and particularly sodium bismuthate and potassium bismuthate. In the process of the reaction, the $Bi^{+5}$ is reduced by any chloride ion to $Bi^{+3}$ and the chloride ion is oxidized to free chlorine. In this way, the chlorine escapes as the free gas.

While the bismuthate ion may be added as an aqueous solution since it has some level of solubility, it is much preferred that it be used in solid form as explained below. Since the bismuthate reaction with chloride ion is believed to be a surface reaction, the reaction is facilitated if the bismuthate, for example, in the form of solid sodium bismuthate, is mixed with a filter aid to increase available surface area of the bismuth compound for reaction with chloride and facilitate flow of the liquid sample through the matrix. Any such filter aid, if used, must be inert to acidified test samples, any chloride present or chlorine generated, and not retain or contribute any organic compounds. Numerous filter aids are available and can be used, but the most preferred are inert high-density glass beads of 40 micron average size. Suitable glass beads are obtained from 3M and sold under the trademark Empore™ 400.

It is preferred that a mixture of the bismuthate ion or pentavalent bismuth source, such as sodium bismuthate, and the inert filter aid be 1:1 on a volume basis. While this is not critical, a 1:1 relationship does seem to perform satisfactorily in that it allows the acidified test sample to freely flow through the solid form bismuthate reagent, while at the same time providing intimate contact. Other ratios have been tested and found to be satisfactory, and may be desirable due to cost or other important factors. It is conceivable that other inert filter aids such as clays like diatomaceous earth, etc., may be employed as well.

The aqueous COD sample is acidified prior to contacting it with the solid form bismuthate or other pentavalent bismuth source. Any non-halogen mineral acid is suitable, such as sulfuric, phosphoric or nitric acids. The acid concentration for sulfuric acid should be within the range of from 3% to 50%, and generally from 8% to 25% is preferred. This corresponds to normalities of from about 1 normal to 18 normal, and preferably from 3 normal to 9 normal. The current procedure operates at about 10% sulfuric acid (approximately 3.5 normal to 4 normal) which is easily obtained by combining 1 part concentrated sulfuric acid, with 9 parts of sample. If the acid is more dilute than about 1 normal, the bismuthate oxidation-reduction reaction will not occur fast enough, and if it is much more concentrated than 18 normal, the bismuthate or pentavalent bismuth will attack organic compounds either directly or through the generation of intermediate oxidizing agents.

Applicant does not wish to be bound by any theory of operation, but notes that it is surprising that chloride is selectively oxidized in the presence of organics which one might also expect to be oxidized but apparently are not. It is believed that the reaction occurs on the surface of the bismuthate compound particles.

The pretreatment step can be conducted in a variety of ways, but the preferred way is in conjunction with the cartridge unit herein described. In this way there is a pretreatment with solid form bismuthate in a manner that does not remove any organics, which of course need to be retained in order to get an accurate COD analysis.

Turning to FIG. 1, it shows the device in perspective and exploded view. The device or composite cartridge unit 10 is comprised of an outer cartridge 12 and an inner cartridge 14. Looking first at outer cartridge 12, it has an open top end 16 and a perforated bottom end 18 joined by circular wall 20 to form a cylindrical shape. Top end 16 has a shoulder portion 22 and rim 24. Positioned over the perforated bottom end 18 is fixed porous filter 26 (see FIG. 2) and held in place in some manner such as a press fit or welded configuration. Positioned on filter 26 is a mixture of solid form bismuthate and filter aid 28. Positioned on or above mixture 28 is a fixed porous filter 30.

The inner cartridge 14 has an open top 32 and a perforated bottom 34, joined by a similar circular wall 36. Positioned on perforated bottom 34 is a removable press fit porous filter 38. The diameter of inner cartridge 14 is such that it can matingly fit inside of the open top 16 of outer cartridge 12 encapsulating the reagent mixture 28 as shown in FIG. 2. Outer cartridge 12 can then be inserted in the top of test tube 40 as illustrated in FIG. 3.

Both outer cartridge 12 and inner cartridge 14 are made of materials that are inert to the acidified sample and reaction products such as chlorine gas. Numerous materials can be employed, but a very suitable inert material is polypropylene. Other polymeric alpha olefins such as polyethylene could also be utilized. The precise material is not critical, as long as it is inert to the acidified sample and reaction products. Filter 38 must additionally be inert to the COD reagent under test conditions (oxidizing acid media at elevated temperature).

In actual operation, the analytical test using the outer and inner cartridges containing the reagent and filters assembled together as a unit 10 is conducted in the following manner. A test sample is mixed with the mineral acid, preferably sulfuric acid, to the concentrations previously specified. The COD test reagent, the prior art dichromate reagent or the Manganese III reagent of the previously incorporated by reference Miller application, is placed in test tube 40. A 0.60 milliliter sample of the aqueous COD material diluted 1:9 with the sulfuric acid solution previously referred to is inserted into the open mouth or top of the previously-described cartridge unit 10. The test tube 40 is then, for example, placed in a centrifuge and centrifuged to draw the acidified aqueous COD sample through press fit filter 38, the perforated bottom 34 of cartridge 14, the fixed filter 30, through the mixture of bismuthate and filter aid 28, through fixed filter 26, perforated bottom 18 of cartridge 12 and down into test reagent 42 in test tube 40. As the acidified aqueous COD sample is pulled through the cartridge unit by centrifugal action, the previously referred to oxidation-reduction reaction occurs. Bismuthate $Bi^{+5}$ is reduced to $Bi^{+3}$ ion, and chloride ($Cl^-$) is oxidized to free chlorine which escapes as a gas. As can be seen, any chloride ion is removed by the process. In order to recover any organics that may have been removed as solid particles by filter 38, it is removed from inner cartridge 14 and added to the reagent 42 in test tube 40. Thereafter the COD analysis occurs in conventional fashion.

The amount of time that the acidified aqueous COD sample is in contact with the reagent in the cartridge must be adequate for the reaction to occur. The amount of time for the centrifugation must be adequate to both allow time for the reaction to occur and for the sample to pass as completely as possible through the cartridge and the reagent it contains. The rate at which the sample flows through the cartridge is also a function of the pore size, thickness and composition of the filters selected for the cartridge unit. Filters composed of glass fiber or polymeric materials have been found to be suitable, provided they are inert to acidified test samples, any chloride present or chlorine generated, and not retain or contribute any organic compounds. A restriction on filter 38 is that it must be inert to the digestion process that occurs in solution 42 in test tube 40. An additional restriction on filters 26 and 30 is that they must be inert to the bismuthate reagent 28.

The rate is also a function of the design of the centrifuge unit, specifically, the radius of the arc traveled by the unit in the test tube and the rate of travel (rpm), which together dictate the g-force on the unit and the sample it contains. When centrifugation is employed, suitable results can be obtained in a fixed time between 1 and 5 minutes, depending on the design of the centrifuge, the rpm setting as previously described and the composition of the filters. An Eppendorf Model 5416 centrifuge gave satisfactory results when samples were spun at 2500 rpm for 3 minutes. Equally satisfactory results were obtained using a 2-step centrifugation process where the first step occurs at a slower speed and duration (500 rpm for 2 minutes) adequate to allow time for the aqueous solution to be in contact with the bismuthate, and a second step which utilizes a higher speed (2500 rpm for 1 minute) to force as much of the aqueous sample out of the cartridge unit and into the test tube as possible. The 2-step centrifugation has different flow requirements than the previously described single-step process, and, hence, uses a different combination of filter materials, typically glass fiber filters only, though some polymer filters may also be acceptable.

Filters 26 and 30 have been described here as separate pieces, but it is possible for both inner cartridge 14 and outer cartridge 12 to have integrally welded filters. With respect to inner cartridge 14, filter 30 would be positioned above perforated bottom end 34 and below press fit filter 38. The preferred method of forcing aqueous COD samples through the cartridge is by centrifugation. Equally satisfactory results were obtained with vacuum filtration. In this method, the sample would be pulled via vacuum through the solid bismuthate. Another alternative is to force the acidified aqueous sample through the cartridge under pressure.

The following examples are offered to further illustrate, but not limit, both the process and the device of the present invention. In the test as outlined below, in order to test efficacy of chloride removal, a blank containing no chloride was used, and thereafter, controls with added amounts of 200 ppm of chloride, 500 ppm of chloride and 1000 ppm of chloride were made. The blank was COD tested using a Hach Company Model DR3000 spectrophotometer and an average value for 9 trials was obtained of 1.470 absorbance. Thereafter, the known test samples containing 200 ppm, 500 ppm and 1000 ppm of chloride were tested. Absorbance readings were thereafter taken. Generally, for the Hach system as the absorbance reading goes down, the COD value increases. Thus, the objective is to keep the reading as close as possible to the blank. If this is accomplished, it shows that the chloride is not interfering to give a false high reading.

In accordance with the process, cartridges were prepared as previously described. Outer cartridge 12 contained 0.2 cubic centimeters of sodium bismuthate mixed with filter aid on a 1:1 volume ratio. Concentrated sulfuric acid, 36 normal, and samples were mixed in a 1:9 ratio, and 0.6 ml of this mixture was pipetted into the inner cartridge 14 of the assembled unit. Thereafter, it was placed in a centrifuge and spun for 2 minutes at 500 rpm followed by 1 minute at 2500 rpm. Thereafter, the press fit filter 38 was taken out and added to the reagent 42 in test tube 40 followed by COD testing using the Hach Model DR 3000 spectrophotometer.

As indicated for the blank sample with 9 trials, the average absorbance value was 1.470. Table I below shows the values of the blank and of five separate measurements for samples containing 200 ppm, 500 ppm and 1000 ppm chloride and one value for each showing the results of testing in the presence of chloride without benefit of the pretreatment process. As can be seen from the table, deviation from the average value for the blank 1.470 was very small as compared to no pretreatment, indicating that chloride had effectively been removed so that there was minimal chloride interference.

TABLE I

| Sample | Absorbance Value | | | | | | Value w/o Pre-Treatment |
|---|---|---|---|---|---|---|---|
| | Value 1 | Value 2 | Value 3 | Value 4 | Value 5 | Avg. | |
| 1 Blank | (9 trials were averaged for this "blank" value) → | | | | | 1.470 | |
| 2 Cl-200 | 1.463 | 1.462 | 1.423 | 1.427 | 1.458 | 1.447 | 1.375 |
| 3 Cl-500 | 1.443 | 1.453 | 1.481 | 1.459 | 1.438 | 1.455 | 1.250 |
| 4 Cl-1000 | 1.435 | 1.426 | 1.425 | 1.423 | 1.437 | 1.429 | 1.075 |

It therefore can be seen that the invention accomplishes at least all of its stated objectives.

What is claimed is:

1. A test cartridge unit for use in measuring the chemical oxygen demand measurement of a treatment sample in conjunction with a sample collection vessel, comprising:

an inner and an outer cartridge, said inner cartridge adapted to matingly fit within said outer cartridge to form the cartridge unit;

each of said inner and outer cartridge having open upper ends and perforated lower ends;

said outer cartridge retaining in solid form a source of bismuthate mixed with an inert filter aid through which a test sample is to move;

said inner cartridge containing a removable filter for collecting suspended particles in the test sample for addition back to the test sample;

said inner and outer cartridge being comprised of polypropylene or polyethylene.

2. The cartridge unit of claim 1 wherein the filter aid is free flowing glass beads.

3. The test cartridge unit of claim 1 wherein the source of bismuthate with an inert filter aid is juxtaposed between fixed porous filters.

* * * * *